United States Patent
Mathis et al.

[11] Patent Number: 6,048,343
[45] Date of Patent: Apr. 11, 2000

[54] BONE SCREW SYSTEM

[76] Inventors: John M. Mathis, 6270 Mt. Chestnut Rd., Roanoke, Va. 24018; Stephen M. Belkoff, 7449 Bradshaw Rd., Kingsville, Md. 21087; Charles J. Phillips, 1203 Cherry Tree La., Annapolis, Md. 21403; Marshall D. Welch, III, 10116 Arapahoe Rd., Lafayette, Colo. 80026; Steven M. Kmiec, 163 Ashbrook Dr., Coventry, Conn. 06238

[21] Appl. No.: 09/324,106

[22] Filed: Jun. 2, 1999

[51] Int. Cl.$^7$ ................................................. A61B 17/58
[52] U.S. Cl. ............................................. 606/72; 606/92
[58] Field of Search ............................... 606/65, 69, 70, 606/71, 72, 73, 67, 92, 93, 94

[56] References Cited

U.S. PATENT DOCUMENTS

| | | |
|---|---|---|
| 4,065,817 | 1/1978 | Branemark et al. . |
| 4,653,487 | 3/1987 | Maale . |
| 4,712,957 | 12/1987 | Edwards et al. . |
| 4,760,844 | 8/1988 | Kyle . |
| 4,860,513 | 8/1989 | Whitman . |
| 5,129,901 | 7/1992 | Decoste . |
| 5,143,498 | 9/1992 | Whitman . |
| 5,145,301 | 9/1992 | Yamamoto . |
| 5,249,899 | 10/1993 | Wilson . |
| 5,253,965 | 10/1993 | Angel . |
| 5,483,781 | 1/1996 | Ernst et al. . |
| 5,725,581 | 3/1998 | Branemark . |
| 5,788,702 | 8/1998 | Draenert . |

Primary Examiner—Michael Buiz
Assistant Examiner—Daphna Shai
Attorney, Agent, or Firm—Rosenberg, Klein & Lee

[57] ABSTRACT

A bone screw system (100) is provided that includes a cannulated bone screw (110) and an adapter (140) designed to be releasably coupled to the screw (110). The screw (110) has a head (112) with an opening (126) formed therein. A shank portion (114) of screw (110) extends from the head (112) and has a closed end bore (124) formed therein in open communication with the opening (126). The screw (110) has a threaded portion (116) in which a plurality of apertures (122) are formed in a root portion (120) of the thread. The adapter (140) has a distal end (150) adapted for releasable coupling with the head (112) and has a passage (162) extending longitudinally therethrough for open communication with the bore (124) of the screw (110). The adapter (140) further includes a grip portion (154) formed by a plurality of spaced annular ridges (156). The proximal end of adapter (140) has a fitting (142) formed thereon for coupling to a device for dispensing a purchase enhancing composition, through the adapter (140) and bore (124) to the apertures (122).

22 Claims, 3 Drawing Sheets

BONE SCREW SYSTEM

BACKGROUND OF THE INVENTION

1. Field of the Invention

The present invention relates in general to threaded fasteners utilized in the medical arts for engagement with bony tissue. More in particular, the present invention is directed to a cannulated bone screw adapted for dispensing a purchase enhancing composition to the threaded portion thereof. Further, the screw of the present invention is cannulated with a closed end bore to prevent the dispensing of a purchase enhancing composition through the distal end of the screw. Still further, the present invention includes an adapter releasably lockingly engageable with the head of the screw on one end thereof and adapted for coupling to a dispenser on the opposing end, wherein the purchase improving composition can be dispensed through the adapter into the screw.

2. Prior Art

Cannulated fastening devices that function in cooperation with the dispensing of an adhesive are well known in the art. Prior art known to the Applicants include U.S. Pat. Nos. 5,143,498; 5,483,781; 5,788,702; 5,725,581; 5,249,899; 4,065,817; 4,653,487; 4,860,513; 5,145,301; 4,712,957; 5,253,965; 4,760,844; and, 5,129,901.

While cannulated bone screws are known in the art, such typically have a passage formed longitudinally therethrough, to thereby allow placement of the screw over a guide wire. Where such screws are utilized with an adhesive composition, in an attempt to increase the purchase of the screw threads, the injection of the adhesive forms a pool at the distal end of the screw, which does little to enhance the purchase of the threads. If the adhesive is injected prior to the setting of the screw in its final position, the screw must move through the pool of adhesive, displacing the adhesive and bone tissue as the screw is tightened, thereby requiring a greater torque to be applied to the screw. The requirement for greater torque is disadvantageous where small or fragile bones are being engaged.

In other fasteners, such as that embodied in U.S. Pat. Nos. 5,249,899, 5,143,498, 4,653,487, and, 4,065,817, dispensing apertures are formed in diametrically apposed positions along the shank of the fastener. The arrangement of diametrically opposed apertures reduces the cross-sectional area of the shank wall, substantially weakening the fastening device. While a broken screw can be tolerated in many applications, such is not acceptable for a bone screw.

SUMMARY OF THE INVENTION

A bone screw system is provided that includes a bone screw having a head adapted to be driven by a tool and a shank portion extending longitudinally from the head. The shank portion has threads formed on at least a portion thereof and a bore extending longitudinally to a closed distal end. The threaded portion has a plurality of apertures formed therein in open communication with the bore. The head has an opening formed therein and in open communication with the bore. The bone screw system further includes an adapter releasably lockingly coupled to the head of the bone screw and sealingly engaged with the bore for injection of a composition therein to pass through the plurality of apertures and thereby aid in fixation of the threads in a patient's bone.

Looking at the instant invention from another aspect, a bone screw system is provided that includes an adapter having a passage formed longitudinally therethrough and a bone screw having a head adapted to be driven by a tool. The bone screw has a shank portion extending longitudinally from the head and has threads formed on at least a portion thereof and a bore extending longitudinally to a closed distal end. The threaded portion has a plurality of apertures formed therein in open communication with the bore. The head has an opening formed therein and in open communication with the bore for receiving a distal end of the adapter therein. The adapter passage is disposed in aligned relationship with the bore. The bone screw system further includes structures for releasably lockingly coupling the distal end of the adapter to the head of the screw.

DESCRIPTION OF THE PREFERRED EMBODIMENTS

Figure 1:
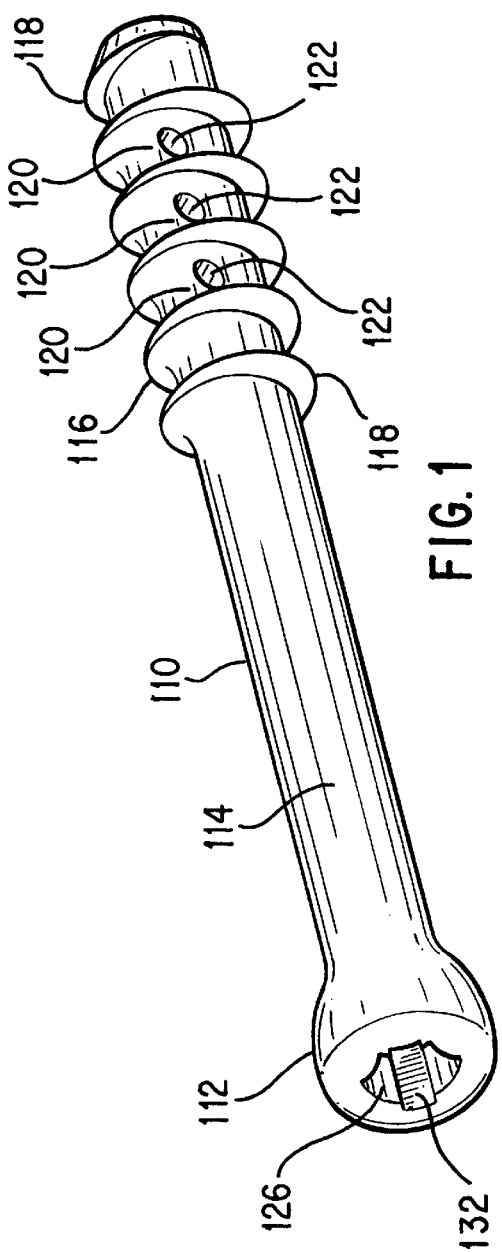
FIG. 1 is a perspective view of the screw of the present invention.
Figure 2:
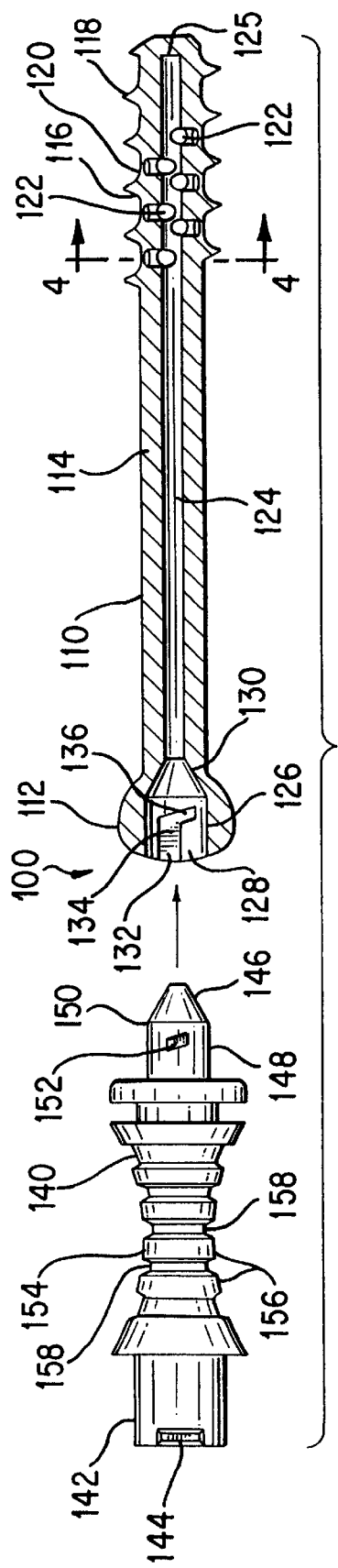
FIG. 2 is an exploded view, partially sectioned, of the bone screw system of the present invention.

Referring to FIGS. 1–4, there is shown, bone screw system 100 for providing fixation in medical applications. In particular, the bone screw system 100 includes a bone screw 110 and an adapter 140 that may be releasably lockingly coupled to the bone screw 110. The adapter provides an interface for injection of a composition intended to improve the purchase of bone screw 110. Bone screw 110 is cannulated by a closed end bore 124 with a plurality of apertures 122 formed through the root portion 120 of the threaded area 116 for dispensing the injected composition therethrough. The composition dispensed through the apertures 122 may be a resin or other adhesive composition that is biocompatible. One such well known biocompatible adhesive resin is methylmethacrelate.

Bone screw 110 includes a head 112 adapted to be driven by a tool. As shown, head 112 includes an hexagonally shaped opening 126 for receiving an Allen type wrench therein. Obviously, other shaped openings may be utilized for rotative coupling to a tool having a complementary contour, or the outer contours of the head may be shaped to receive a driving tool thereon. Extending distally from the head 112, there is a shank portion 114 having at least a threaded portion 116 formed thereon. Threaded portion 116 is formed with thread crests 118 helically disposed on the shank 114, with the root portion of the threads being helically disposed between adjacent thread crests 118. As shown, threaded portion 116 occupies a distal end portion of the shank 114. The extent of shank 114 having threads is a function of the application for which the screw 110 is being used and may occupy a 10%–100% portion of the shank 114.

Extending through the shank portion 114 is a bore 124, the bore extending longitudinally to a closed distal end 125. The opening 126 of head 112 is disposed in open communication with the bore 124, so that the composition that is injected can pass into the bore 124. A plurality of apertures 122 are formed in the root portion of the threads, and are formed in open communication with the bore 124. Therefore, when the composition is injected into the bore 124, such flows out through the apertures 122.

The apertures 122 extend radially outward from the central bore 124, and are spaced one from another by an angle θ, while being longitudinally displaced, one from another, as a function of the slope of the helical path of the root portion 120 of the thread. It has been found that an optimal combination of dispersion of the injected composition and wall cross-sectional area occurs when there are three apertures per screw revolution, 360 angular degrees. Where the apertures 122 are uniformly spaced, the apertures ace located at 120° intervals. The apertures 122 may be spaced at other angles, as long as they are not located in a diametrically opposing location. The apertures 122 are displaced longitudinally one from another, following the helical contour of the thread root 120. By that arrangement, none of the apertures 122 are diametrically opposed from another aperture 122. With the apertures 122 not being diametrically opposed, there is a minimal reduction in cross-sectional area of any particular longitudinal location of the threaded portion 116, which is a critically important characteristic.

Injection of the purchase enhancing composition requires the dispensing of the composition under pressure into the bore 124 of bone screw 110. In order to accomplish the pressurized injection of the composition into bore 124, adapter 140 is provided. Adapter 140 is provided with a distal end 150 which is insertable into the opening 126 of the bone screw head 112. The opposing proximal end of adapter 140 has a fitting for fluid connection formed thereon. Where the purchase enhancing composition is to be dispensed from hypodermic-type syringes, the fitting 142 formed an the proximal end of adapter 140 is a luer-type connection, having a conically tapered portion 164 formed therein. Further, the fitting 142 may include a pair of opposing lugs 144 for releasable coupling with a mating luer-lock type fitting.

The distal end 150 of adapter 140 includes a conically shaped external surface 146 which sealingly mates with a respective conically shaped internal surface 130 formed at the distal end of opening 126, adjacent the bore 124. A portion 148 of distal end 150, adjacent to the conically-shaped surfaced 146, is formed with a pair of opposing locking lugs 152 extending therefrom. Locking lugs 152 provide for releasable coupling within respective recesses 132 formed in opposing interior wall surfaces of the opening 126. More specifically, the recesses 132 are formed in the proximal portion 128 of opening 126. Each of the recesses 132 includes a longitudinally directed section 134 for guiding displacement of the locking lugs 152 responsive to insert of the adapter distal end 150 into the opening 126 in the bone screw head 112. At the distal end of the longitudinally directed section 134, there is formed an angularly directed section 136, the section 136 being angled toward the distal end of the screw 110. As the locking lugs 152 are disposed on an incline to mate with the angularly directed section 136 of recess 132, rotation of the adapter 140 longitudinally displaces the adapter 140. The conically shaped portion 146 of the adapter distal end 150 is thereby tightly engaged with the conically shaped internal surface 130 of opening 126, providing a seal therebetween. By that arrangement, the passage 162 of adapter 140 is placed in open communication with the bore 124 of screw 110. Thus, with adapter 140 coupled to screw 110, fluid communication is established between a dispensing device coupled to fitting 142 and the plurality of apertures 122.

Figure 1A:
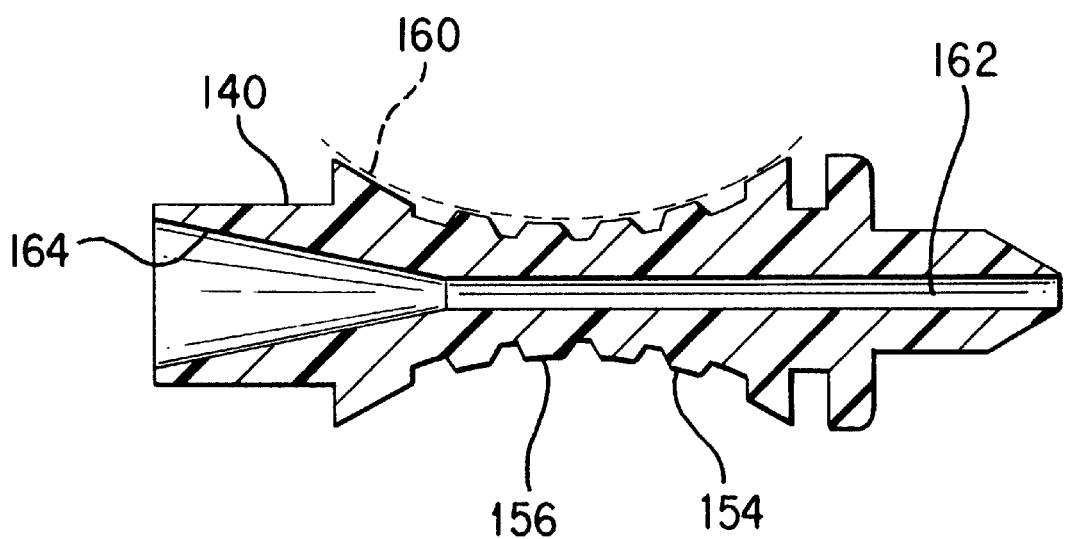
FIG. 1A is a cross-sectional view of the adapter of the present invention.
Figure 3:
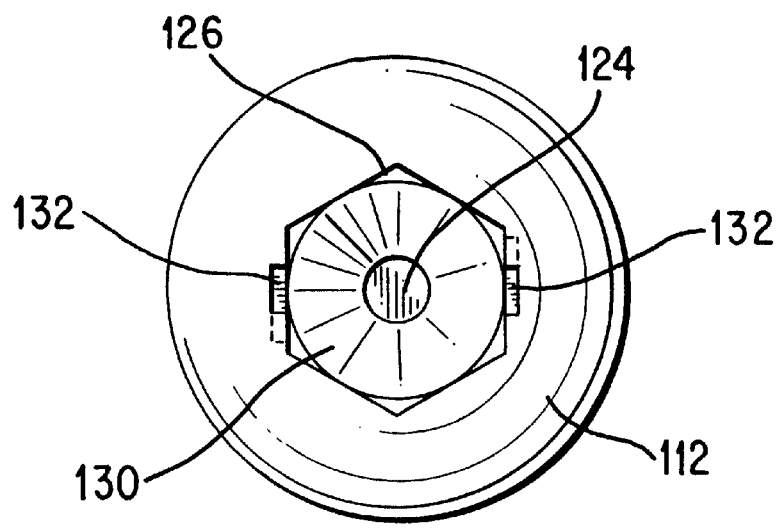
FIG. 3 is a proximal end view of the screw of the present invention.
Figure 4:
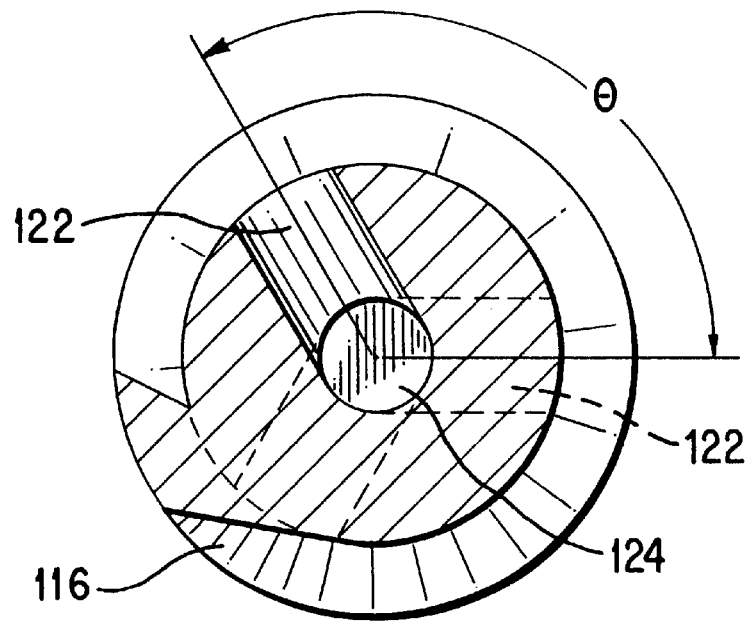
FIG. 4 is a cross-sectional view of the screw of the present invention taken along the section line 4—4 of FIG. 2.

Adapter 140 is formed with a grip portion 154 disposed intermediate the opposing ends thereof. Grip portion 154 is formed with a plurality of annular ridges disposed in longitudinally spaced relationship. Each of the annular ridges 156 are separated by a respective groove 158, to thereby increase the grippable surface area of the adapter grip portion 154. The plurality of annular ridges 156 need not be of the same diameter. In order to further enhance the gripping contact area, the plurality of annular ridges 156 are dimensioned to collectively define an arcuate longitudinal cross-sectional contour, as indicated by the contour line 160 shown in FIG. 1A, providing a depression in the adapter's surface for receiving the user's fingers therein. That arrangement of the gripping portion 154 allows a physician to easily engage and disengage the adapter from the screw 110.

Bone screw system 100 includes a bone screw 110 and an adapter 140 having a distal end 150 that is releasably lockingly coupled to the head 112 of bone screw 110 for dispensing a purchase improving composition supplied to the proximal end of the adapter 140. The conically shaped external surface 146 formed on the distal end 150 of adapter 140 is forced into sealing engagement with the corresponding conically shaped internal surface 130 of the opening 126. The sealing engagement is established by the insertion and rotation of the distal end 150 of adapter 140 within the opening 126. The locking lugs 152 pass through the longitudinally directed section 134 of respective recesses 132 as the distal end 150 is inserted into the opening 126, and respectively follow the angularly directed section as the adapter 140 is rotated.

Further, the strength of the cannulated screw 110 is maintained by limiting the number of apertures 122 formed in the threaded portion 116, and forming such in both angular and longitudinal spaced relationship, in the helically directed root portion 120 of the thread. The apertures being both angularly and longitudinally displaced one from another, minimizes the reduction in cross-sectional area of the wall surrounding the centrally disposed bore 124, which is of critical importance. In particular, the dispensing of adhesive onto the threads of the screw and the minimization of cross-sectional area reduction is achieved with three apertures within any 360 angular degree section of the threaded portion 116. While an angular spacing θ of 120° has been illustrated, to provide equidistantly spaced apertures, it should be understood that other angular spacings may be utilized. Further, more than three apertures may be utilized in a 360 angular degree section, if the screw pitch is sufficient such that there are no apertures in diametrically opposed locations, minimizing any further reduction in the cross-sectional area of the annular wall of the shank 114.

The adapter 140 is formed with a grip portion 154 having an arcuate longitudinally directed arcuate outer surface contour defined by a mathematical arcuate envelope established by the plurality of annular ridges 156 spaced one from another by respective grooves 158. The arcuate envelope is formed by the combination of ridge apexes, where the respective diameters of the ridges 156 are not uniform. The respective diameters vary in order to collectively form a longitudinally directed arcuate outer surface contour.

The adapter 140 includes a passage 162 extending longitudinally therethrough. The proximal end of the passage 162 may include a conically tapered portion 164 for mating with a complementary conical surface of a connector or other device for dispensing a selected composition through adapter 140 into screw 110. Through the use of system 100, the bone screw 110 can be set and an adhesive dispensed from the threaded portion in a radial direction for improving the purchase of the screw threads, and thereby avoid the problems associated with dispensing adhesive from a distal end of a bone screw.

Although this invention has been described in connection with specific forms and embodiments thereof, it will be appreciated that various modifications other than those discussed above may be resorted to without departing from the spirit or scope of the invention. For example, equivalent elements may be substituted for these specifically shown and described, certain features may be used independently of other features, and in certain cases, particular locations of elements may be reversed or interposed, all without departing from the spirit or scope of the invention as defined in the appended Claims.

What is being claimed is:

1. A bone screw system, comprising:
a bone screw having a head adapted to be driven by a tool and a shank portion extending longitudinally from said head, said shank portion having threads formed on at least a portion thereof and a bore extending longitudinally to a closed distal end, said threaded portion having a plurality of apertures formed therein in open communication with said bore, said head having an opening formed therein and in open communication with said bore; and,
an adapter releasably lockingly coupled to said head of said screw and sealingly engaged with said bore for injection of a composition therein to pass through said plurality of apertures and thereby aid in fixation of said threads in a patient's bone.

2. The bone screw system as recited in claim 1 where said plurality of apertures are respectively formed in a root portion of said threads and spaced at increments of 120°.

3. The bone screw system as recited in claim 1 where said adapter includes a pair of opposing locking lugs extending therefrom adjacent a distal end thereof.

4. The bone screw system as recited in claim 3 where said opening in said head has a pair of recesses formed in opposing interior wall surfaces thereof and extending from a proximal end of said head for respectively receiving said locking lugs therein.

5. The bone screw system as recited in claim 4 where each of said pair of recesses has a longitudinally directed section for guiding displacement of said locking lugs responsive to insert of said adapter distal end into said opening in said head, and an angularly directed section to provide releasable locking engagement with said locking lugs.

6. The bone screw system as recited in claim 1 where said opening in said head has a substantially conically shaped interior surface portion adjacent to said bore.

7. The bone screw system as recited in claim 6 where said adapter has a substantially conically shaped external distal end surface corresponding to said conically shaped internal surface portion of said opening in said head to provide sealing engagement therebetween.

8. The bone screw system as recited in claim 6 where said adapter includes a pair of opposing locking lugs extending therefrom adjacent said conically shaped external distal end surface thereof.

9. The bone screw system as recited in claim 8 where said opening in said head has a pair of recesses extending from a proximal end of said opening and formed in opposing interior wall surfaces thereof adjacent said conically shaped internal surface portion for respectively receiving said locking lugs therein.

10. The bone screw system as recited in claim 9 where each of said pair of recesses has a longitudinally directed section for guiding displacement of said locking lugs responsive to insert of said adapter distal end into said opening in said head, and an angularly directed section to provide releasable locking engagement with said locking lugs and provide said sealing engagement between said conically shaped surfaces.

11. The bone screw system as recited in claim 10 where said adapter includes a luer-type coupling on a proximal end thereof.

12. The bone screw system as recited in claim 11 where said adapter includes a grip section disposed intermediate said proximal and distal ends thereof.

13. The bone screw system as recited in claim 12 where said grip section is formed with a plurality of annular ridges.

14. The bone screw system as recited in claim 12 where said plurality of annular ridges collectively form a longitudinally directed arcuate outer surface contour.

15. The bone screw system as recited in claim 1 where said adapter includes a grip section disposed intermediate opposing ends thereof.

16. The bone screw system as recited in claim 15 where said grip section is formed with a plurality of annular ridges.

17. The bone screw system as recited in claim 16 where said plurality of annular ridges collectively form a longitudinally directed arcuate outer surface contour.

18. A bone screw system, comprising:
an adapter having a passage formed longitudinally therethrough;
a bone screw having a head adapted to be driven by a tool and a shank portion extending longitudinally from said head, said shank portion having threads formed on at least a portion thereof and a bore extending longitudinally to a closed distal end, said threaded portion having a plurality of apertures formed therein in open communication with said bore, said head having an opening formed therein and in open communication with said bore for receiving a distal end of said adapter therein, said adapter passage being disposed in aligned relationship with said bore; and,
means for releasably lockingly coupling said distal end of said adapter to said head of said screw.

19. The bone screw system as recited in claim 18 where said releasable locking means includes a pair of opposing locking lugs extending from an external surface of said adapter adjacent said distal end thereof, and a pair of recesses formed in opposing interior wall surfaces of said opening in said head for respectively receiving said locking lugs therein.

20. The bone screw system as recited in claim 18 where said adapter includes a grip section disposed intermediate opposing ends thereof.

21. The bone screw system as recited in claim 18 where said adapter includes a luer-type coupling on a proximal end thereof.

22. The bone screw system as recited in claim 1 where said opening in said head has a substantially conically shaped interior surface portion adjacent to said bore and said adapter has a substantially conically shaped external distal end surface corresponding to said conically shaped internal surface portion of said opening in said head to provide sealing engagement therebetween.

* * * * *

(12) EX PARTE REEXAMINATION CERTIFICATE (9505th)
United States Patent
Mathis et al.

(10) Number: US 6,048,343 C1
(45) Certificate Issued: Feb. 8, 2013

(54) BONE SCREW SYSTEM

(75) Inventors: John M. Mathis, Roanoke, VA (US); Stephen M. Belkoff, Kingsville, MD (US); Charles J. Phillips, Annapolis, MD (US); Marshall D. Welch, III, Lafayette, CO (US); Steven M. Kmiec, Coventry, CT (US)

(73) Assignee: Stryker Corporation, Kalamazoo, MI (US)

Reexamination Request:
No. 90/012,169, Mar. 9, 2012

Reexamination Certificate for:
Patent No.: 6,048,343
Issued: Apr. 11, 2000
Appl. No.: 09/324,106
Filed: Jun. 2, 1999

(51) Int. Cl.
*A61B 17/88* (2006.01)
*A61B 17/68* (2006.01)
*A61B 17/86* (2006.01)

(52) U.S. Cl. ........... 606/916; 606/304; 606/308; 606/92
(58) Field of Classification Search .................. None
See application file for complete search history.

(56) References Cited

To view the complete listing of prior art documents cited during the proceeding for Reexamination Control Number 90/012,169, please refer to the USPTO's public Patent Application Information Retrieval (PAIR) system under the Display References tab.

*Primary Examiner* — David O. Reip

(57) ABSTRACT

A bone screw system (100) is provided that includes a cannulated bone screw (110) and an adapter (140) designed to be releasably coupled to the screw (110). The screw (110) has a head (112) with an opening (126) formed therein. A shank portion (114) of screw (110) extends from the head (112) and has a closed end bore (124) formed therein in open communication with the opening (126). The screw (110) has a threaded portion (116) in which a plurality of apertures (122) are formed in a root portion (120) of the thread. The adapter (140) has a distal end (150) adapted for releasable coupling with the head (112) and has a passage (162) extending longitudinally therethrough for open communication with the bore (124) of the screw (110). The adapter (140) further includes a grip portion (154) formed by a plurality of spaced annular ridges (156). The proximal end of adapter (140) has a fitting (142) formed thereon for coupling to a device for dispensing a purchase enhancing composition, through the adapter (140) and bore (124) to the apertures (122).

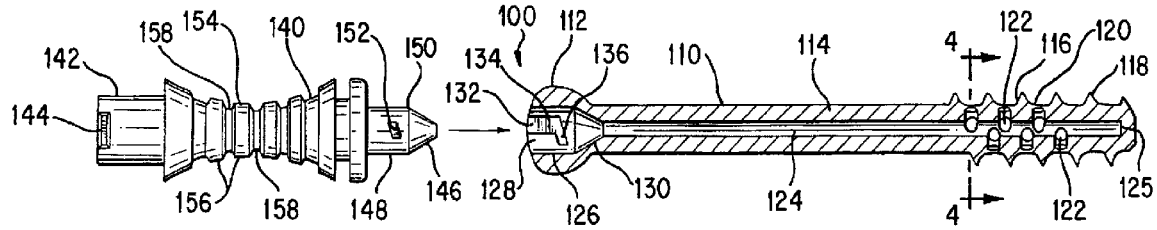

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claim 1 is cancelled.

Claims 2-22 were not reexamined.

* * * * *